US00RE35987E

United States Patent [19]

Harris et al.

[11] E Patent Number: Re. 35,987

[45] Reissued Date of Patent: Dec. 8, 1998

[54] OUTPUT PULSE COMPENSATION FOR THERAPEUTIC-TYPE ELECTRONIC DEVICES

[75] Inventors: Frank W. Harris, Boulder; Alan R. Owens, Longmont, both of Colo.

[73] Assignee: Staodyn, Inc., Longmont, Colo.

[21] Appl. No.: 385,285

[22] Filed: Feb. 8, 1995

Related U.S. Patent Documents

Reissue of:

[64] Patent No.: 5,184,617
Issued: Feb. 9, 1993
Appl. No.: 533,293
Filed: Jun. 5, 1990

[51] Int. Cl.[6] ..... A61N 1/08

[52] U.S. Cl. ..... 607/63; 607/72

[58] Field of Search ..... 607/72, 63, 2, 607/46, 48

[56] References Cited

U.S. PATENT DOCUMENTS

| | | | |
|---|---|---|---|
| 2,263,205 | 11/1941 | Conrad . | |
| 2,808,826 | 1/1957 | Reiner et al. . | |
| 3,241,557 | 3/1966 | Masaki | 128/422 |
| 3,645,267 | 2/1972 | Hagfors | 128/421 |
| 3,842,844 | 10/1974 | Alferness | 128/422 |
| 3,901,247 | 8/1975 | Walmsley | 128/422 |
| 3,908,669 | 9/1975 | Man et al. | 128/422 |
| 4,014,347 | 3/1977 | Halleck et al. . | |
| 4,088,141 | 5/1978 | Niemi | 128/421 |
| 4,141,359 | 2/1979 | Jacobsen et al. | 128/419 R |
| 4,177,819 | 12/1979 | Kofsky et al. | 128/422 |
| 4,210,151 | 7/1980 | Keller, Jr. . | |
| 4,340,063 | 7/1982 | Maurer . | |
| 4,372,319 | 2/1983 | Ichinomiya et al. | 128/421 |
| 4,431,002 | 2/1984 | Maurer et al. . | |
| 4,453,548 | 6/1984 | Maurer et al. . | |
| 4,520,825 | 6/1985 | Thompson et al. | 128/422 |
| 4,539,993 | 9/1985 | Stanton | 128/421 |
| 4,759,368 | 7/1988 | Spanton et al. . | |
| 4,926,865 | 5/1990 | Oman | 128/421 |
| 4,979,507 | 12/1990 | Heinz et al. | 128/419 PG |

FOREIGN PATENT DOCUMENTS

| | | |
|---|---|---|
| 0269844 | 10/1987 | European Pat. Off. . |
| 0269848 | 10/1987 | European Pat. Off. . |
| 0339313 | 5/1989 | European Pat. Off. . |
| 2504807 | 4/1981 | France . |
| 2526180 | 5/1983 | France . |
| 2528709 | 6/1983 | France . |
| 2336286 | 11/1983 | France . |
| 8602567 | 5/1986 | WIPO . |

*Primary Examiner*—William E. Kamm
*Assistant Examiner*—Kennedy J. Schaetzle
*Attorney, Agent, or Firm*—Robert G. Crouch

[57] ABSTRACT

Pulse compensation is disclosed for electronic devices capable of producing a pulse output signal suitable for therapeutic purposes with pulse compensation being automatically provided upon sensing of a change in she conditions being monitored. The electronic device, which preferably includes a microcomputer, has externally accessible pulse width and intensity controls for determining the width and amplitude of pulses then being delivered. Upon each sensing of a change in a monitored condition capable of causing user discomfort or possible injury, the intensity of the pulses then being delivered is quickly reduced and then gradually increased toward the full intensity requested by the intensity control. Pulse compensation is also provided when the pulse width is varied by the pulse width control to thereby automatically cause a corresponding change in the range of intensities of the pulses then delivered, based upon a nerve fiber strength-duration curve or the pulses, to thereby maintain the stimulation capability of the pulses substantially constant at a percentage of intensity as determined by the intensity control.

27 Claims, 8 Drawing Sheets

OUTPUT PULSE COMPENSATION FOR THERAPEUTIC-TYPE ELECTRONIC DEVICES

Matter enclosed in heavy brackets [ ] appears in the original patent but forms no part of this reissue specification; matter printed in italics indicates the additions made by reissue.

FIELD OF THE INVENTION

This invention relates to an electronic device for producing a pulse output signal for therapeutic purposes, and, more particularly, relates to output pulse compensation for such a device.

BACKGROUND OF THE INVENTION

Electronic devices capable of providing a pulse output signal for therapeutic purposes are now well known, and such devices are known, for example, to include transcutaneous electrical nerve stimulating (TENS) devices and muscle stimulating devices. It is also well known that such devices commonly include externally accessible controls for effecting parameter changes, including changes in pulse width and intensity of the delivered pulses (see, for example, U.S. Pat. No. 4,014,347).

Conventional TENS and muscle stimulator devices commonly use constant current feedback to regulate the charge per pulse. The feedback signal, representing the peak current, is compared with the reference voltage to establish the height of the rectangular pulses, and the reference voltage is usually derived from a variable control device, such as a potentiometer, which serves to control the stimulation intensity. In other words, stimulation amplitude is commonly controlled by varying the peak current of the rectangular current pulses.

It has been found that, at least with respect to TENS devices and muscle stimulator devices, that large pulse widths are useful for short term stimulation since they are more comfortable to the user than narrow pulse width for the stimulation of large muscles. Conversely, narrow pulse widths are more comfortable to the user for stimulating small muscle groups, and narrow pulse widths are particularly well suited for use for long term stimulation which often occurs, for example, in effective stimulation by a TENS unit.

It is usually necessary, or at least desirable, that the pulse width be tuned (i.e., varied) while using the unit. However, since the charge per pulse varies directly with the pulse width, unless the peak current is also adjusted whenever the pulse width is changed, the charge per pulse will also change.

Since stimulation intensities perceived by a user are approximately proportional to the delivered charge per pulse, a wide pulse will acquire a large amount of charge when the intensity control is moved only slightly in the intensity increase direction. Conversely, when the pulse width is narrow, changing the peak current a small amount, by moving the intensity control in the intensity increase direction, will produce a small amount of increase in the charge per pulse. Since pulse width affects the sensitivity of the intensity control where both are utilized in a device, using a pulse width, for example, of greater than about 200 microseconds, causes conventional amplitude controls to become overly sensitive. As a result, pulse widths greater than about 200 microseconds are difficult to control with an ordinary potentiometer-type amplitude, or intensity, control.

In addition, the pulse width of the pulses being delivered sometimes causes confusion with respect to the amount of charge being delivered, or at least perceived to be delivered. For example, if the pulse is 100 ma peak and 200 microseconds wide, the pulse contains 20 microcoulombs charge. While such a charge would normally be too strong to be tolerated with small electrodes such as are commonly used with TENS units, for example, such a charge could easily and safely be tolerated with comfort if sufficiently large electrodes are utilized (i.e., the area of application is made sufficiently greater).

It was therefore found that if the intensity was increased as the pulse width was decreased, and if the intensity was decreased as the pulse width was increased, the charge delivered by the pulses can be controlled to produce a more constant level of stimulation. A strength-duration curve to effect this end was suggested in connection with a diagnostic apparatus (see, U.S. Pat. No. 2,808,826), and has also been suggested for use in connection with TENS units (see U.S. Pat. Nos. 4,431,002 and 4,453,548). In addition, such a curve has been suggested for use in connection with mechanical coupling of pulse width and amplitude controls in a stimulator (see U.S. Pat. No. 4,340,063), such a curve has been suggested for use in connection with scanning output parameters through predetermined ranges to periodically achieve optimum stimulating currents (see U.S. Pat. No. 4,210,151), and such a curve has also been suggested for use in conjunction with strength-duration-rate modulation in a TENS device (see U.S. Pat. No. 4,759,368).

It has also been heretofore suggested that the intensity of the delivered output pulses can be controlled, and gradual increase in such intensity is utilized, for example, in the NuWave® TENS unit now being sold by the assignee of this invention.

Thus, while pulse compensation has heretofore been suggested in connection with therapeutic-type devices, improvements and/or additions to such devices could further improve such devices.

SUMMARY OF THE INVENTION

This invention provides improved output pulse compensation for therapeutic-type electronic devices. Output pulse compensation is automatically provided upon sensing of predetermined changed conditions being monitored, and such compensation is preferably accomplished using a micro-computer in devices constructed according to this invention.

When such a changed condition is sensed that is capable of causing user discomfort, or possible injury, the intensity of the pulses then being delivered is quickly reduced and then gradually increased to the full then requested intensity (unless intensity reduction is again effected due to sensing of a condition being monitored) to thus provide a soft-start.

Upon sensing a change in pulse width initiated by a change of the pulse width control, a predetermined corresponding change in the range of intensities of the pulses then delivered is also effected, based upon the nerve fiber strength-duration curve of the pulses, to thereby maintain the charge delivered per pulse substantially constant, with the percentage of intensity of each pulse being also maintained substantially constant unless a change in percentage is initiated by an intensity control that operates independently of the pulse width control.

It is therefore an object of this invention to provide improved output pulse compensation for a therapeutic-type electronic device.

It is another object of this invention to provide improved proved output pulse compensation that is automatically provided upon sensing of a predetermined changed condition being monitored.

It is still another object of this invention to provide improved output pulse compensation by quickly reducing the intensity of pulses then being delivered upon sensing of a monitored condition capable of causing discomfort or injury, and then gradually increasing the intensity to the requested intensity unless again caused to be reduced due to sensing of a monitored condition.

It is another object of this invention to provide improved output pulse compensation for a therapeutic-type electronic device utilizing a change in the range of intensities corresponding in a predetermined manner to a change in pulse width.

It is another object of this invention to provide improved pulse compensation for therapeutic-type electronic device wherein a change in the range of intensities, corresponding in a predetermined manner to a change in pulse width, is based upon a nerve fiber strength-duration curve.

It is still another object of this invention to provide improved pulse compensation for a therapeutic-type electronic device utilizing a change in the range of intensities, corresponding in a predetermined manner to a change in pulse width, to thereby maintain the charge delivered per pulse substantially constant.

It is yet another object of this invention to provide improved compensation for a therapeutic-type electronic device utilizing a micro-computer to sense monitored conditions and cause output pulse intensity changes in response thereto.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

In this invention, output pulse compensation is automatically provided for a therapeutic-type electronic device when a predetermined change is sensed to occur in a condition being monitored. This includes, for example, monitoring of conditions to prevent user discomfort, or possible injury, due to delivery of output pulses at undesirably high intensity levels, as well as monitoring variations imposed by the user, as, for example, varying the requested pulse width of the pulses to be delivered.

Users have been found to be occasionally startled or even shocked by improper use of nerve stimulators or by defective stimulation units. These incidents are normally characterized by a sudden, perceived increase in the stimulation intensity that surprises the user, and can happen in a number of different ways, including, for example, an abrupt increase in the intensity caused by a requested increase by the intensity control or by a sudden increase in intensity occasioned by battery replacement, loose or intermittent electrode leads, rapid switching between modes, and/or defects causing the device to be reset accidently.

In this invention, monitored conditions are sensed, or detected, preferably using a micro-computer having appropriate algorithms. The algorithms eliminate surprise, and prevent discomfort or possible injury, by resetting the stimulation intensity of the output pulses being then delivered to a low (or zero) level, and then gradually increasing the stimulation intensity up to the level requested by the setting of the intensity control.

Figure 1:
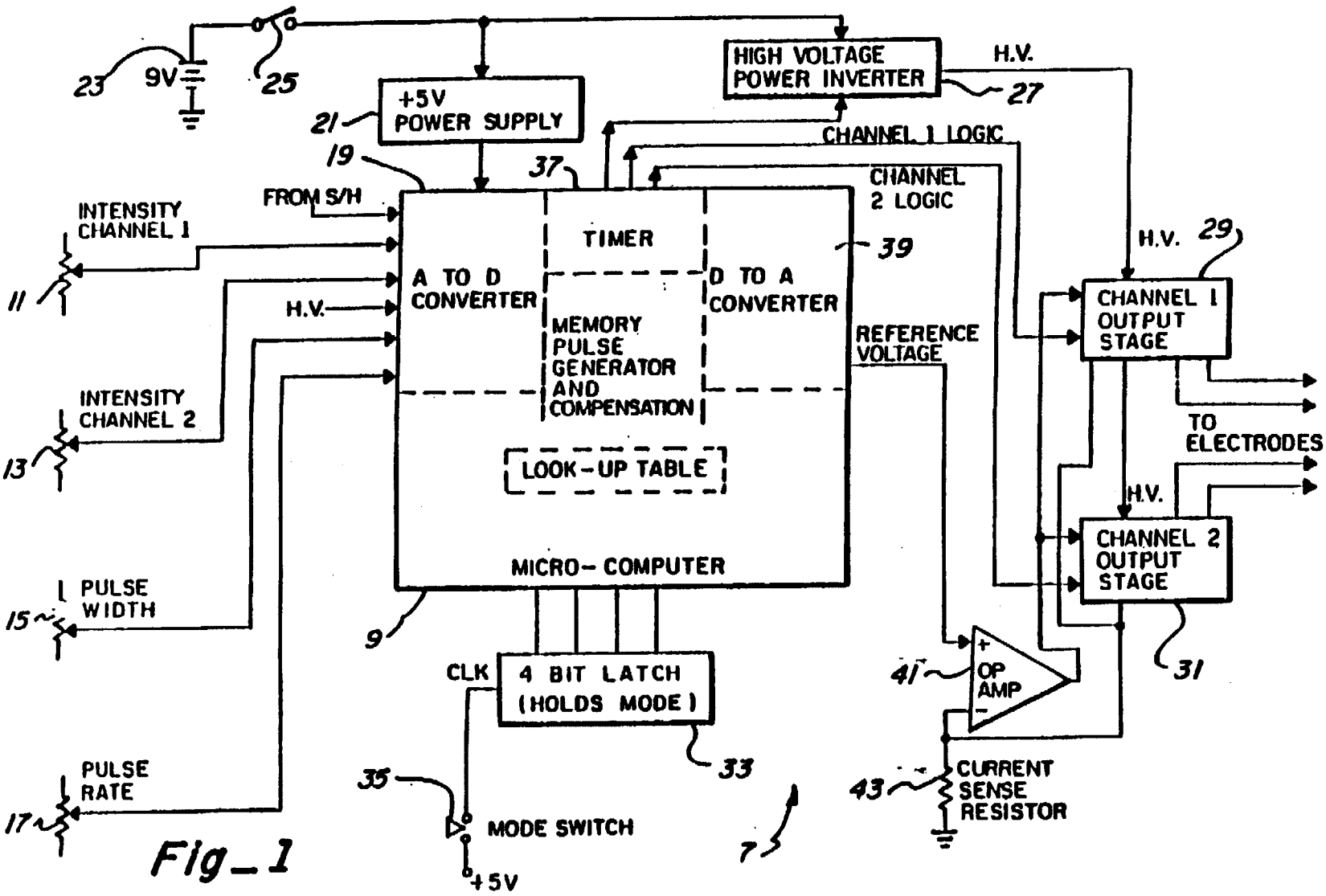
FIG. 1 is a block diagram of a TENS unit having output pulse compensation according to this invention supplied by a micro-computer included as a part of the TENS unit.

Output pulse compensation, according to this invention, is illustrated in FIG. 1 in connection with a TENS device. It is meant to be appreciated, however, that such compensation can be effected with other therapeutic-type devices in the same manner. The TENS device illustrated in FIG. 1 is a plural channel device, but it is meant to be realized that a single channel device could also be utilized.

Referring now to FIG. 1, TENS device 7 includes micro-computer, or controller, 9 that receives an input indicative of intensity, or amplitude, from amplitude control potentiometers 11 and 13 (if plural channels are utilized) and an input indicative of pulse width from pulse width control potentiometer 15. In addition, TENS device 7 can also receive an input indicative of pulse rate from pulse rate control potentiometer 17, as is conventional.

As indicated in FIG. 1, the control inputs (from potentiometers 11, 13, 15 and 17) are coupled to microcomputer 9 (which preferably includes analog-to-digital (A/D) converter 19). Micro-computer 9 is connected with power supply 21 (5 volts), and power supply 21 is connected to battery 23 (9 volts) through on-off switch 25. Battery 23 also provides power to high voltage power inverter 27, which inverter supplies high voltage to the output stages 29 and 31 (if plural channels are utilized), as is conventional for TENS units. The output stage, or stages, are preferably conventional asymmetric biphasic, but can also be symmetrical biphasic.

As also indicated in FIG. 1, a multi-mode operation can be established for the device using latch 33 (a 4 bit latch), to hold the then selected mode, and mode switch 35.

As is conventional, micro-computer 9 generates pulses for each channel utilized (using appropriate algorithms in connection with timer 37, which timer is preferably a part of the micro-computer), and these pulses are coupled to the output stage, or stages, to enable the pulse output signals to be conventionally provided by the device.

As also shown in FIG. 1 micro-computer 9 has also included therein output pulse compensation algorithms and a look-up table with the output being coupled through digital-to-analog (D/A) converter 39 (also preferably a part of micro-computer 9 as shown in FIG. 1). Converter 39 supplies a reference voltage to one input of operational amplifier 41. The other input of operational amplifier 41 is connected with current sense resistor 43, and the output of operational amplifier 41 is coupled to the output stage, or stages. 29 and 31.

Figure 2:
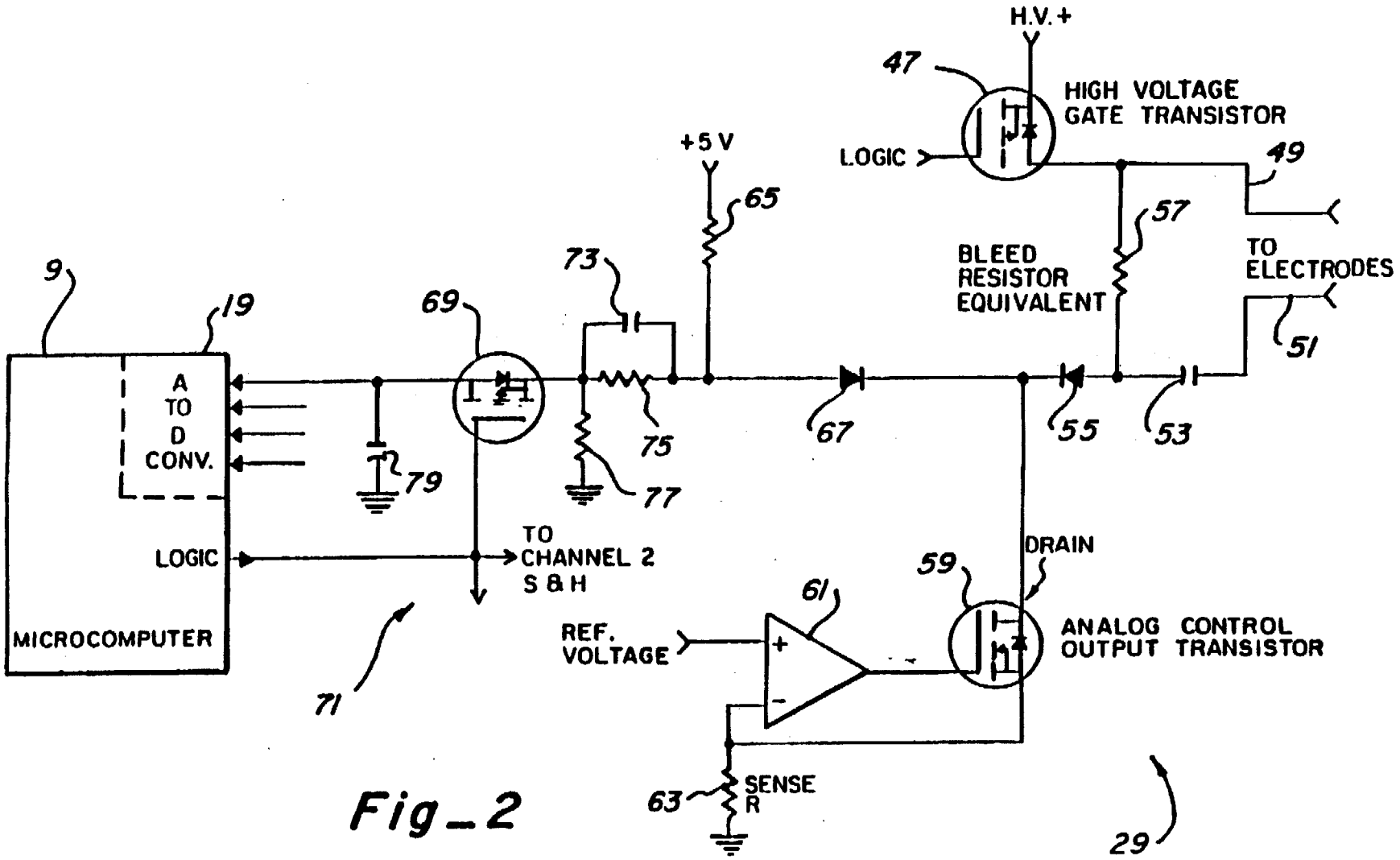
FIG. 2 is a schematic diagram illustrating an output stage as shown in FIG. 1.

Output stages 29 and 31 may be identical and output stage 29 is shown in detail in FIG. 2. As shown, the high voltage is coupled to high voltage gate transistor 47 of output stage 29, and transistor 47 also receives the pulse logic input from micro-computer 9. The output pulses are delivered to a user through lead 49, with the return path from the user being through lead 51, capacitor 53, and diode 55 (with lead 49 being connected to the junction of capacitor 53 and diode 55 through bleed resistor 57).

As also shown in FIG. 2, analog control transistor 59 is connected with the output of operational amplifier 61. Amplifier 61 has one input connected to receive a reference voltage and the other input connected with transistor 59 and is connected with ground through sense resistor 63.

As also shown, a +5 volt power supply is connected to one side of resistor 65. The other side of resistor 65 is connected to one side of diode 67, with the other side of diode 67 being connected to the junction of diode 55 and transistor 59. Gate transistor 69 of sample and hold circuit 71 is connected with the junction of resistor 65 and diode 67 through parallel-connected capacitor 73 and resistor 75 (having resistor 77 to ground connected therewith). The pulse logic from micro-computer 9 is also coupled to transistor 69, and the output from transistor 69 is stored in capacitor 79, which capacitor is connected with A/D convertor 19 of micro-computer 9.

Figure 3:
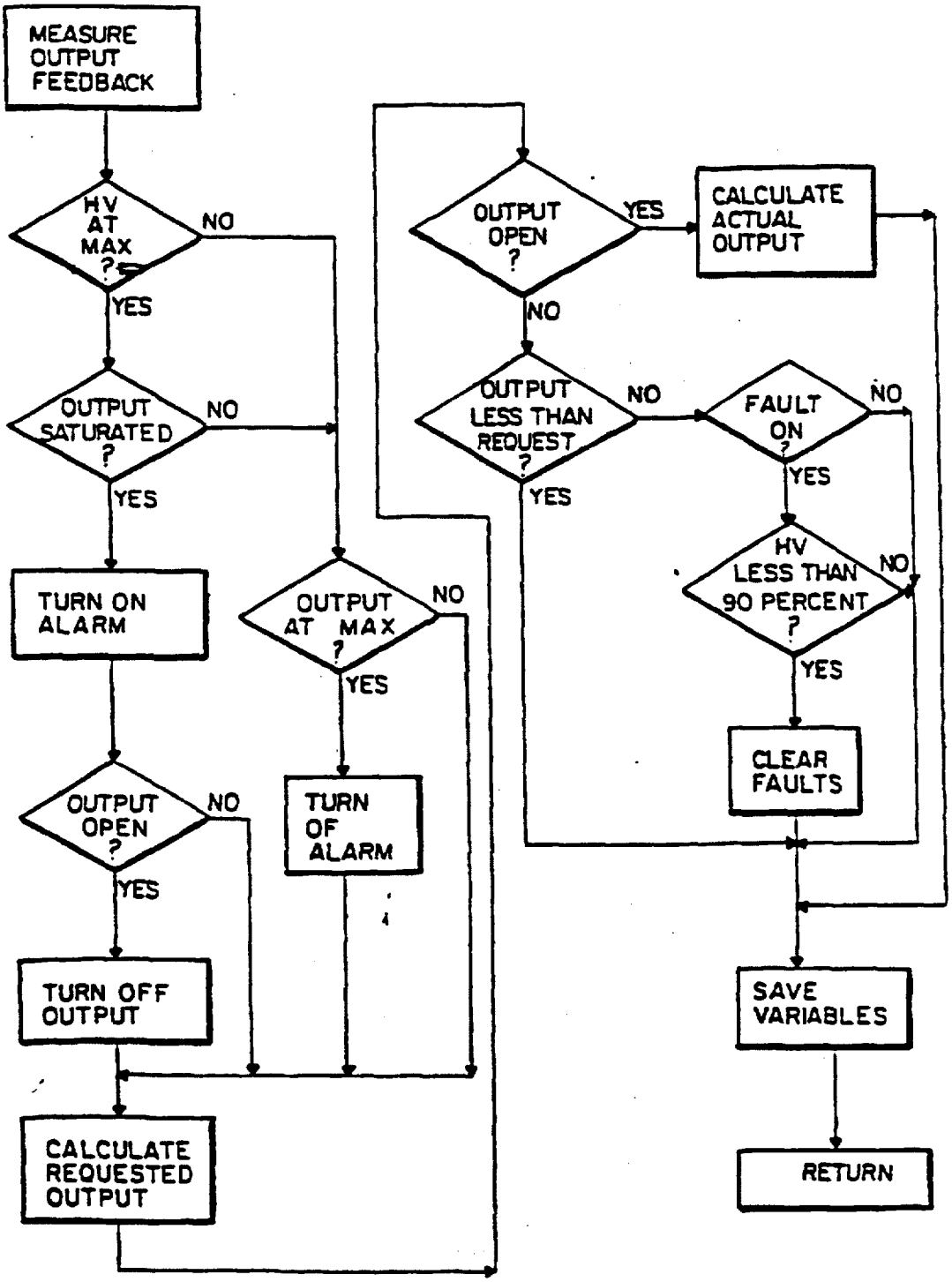
FIGS. 3 through 5 are flow charts illustrating operation of the micro-computer shown in FIG. 1 to control the intensity of the output pubes in response to monitored conditions.
Figure 4:
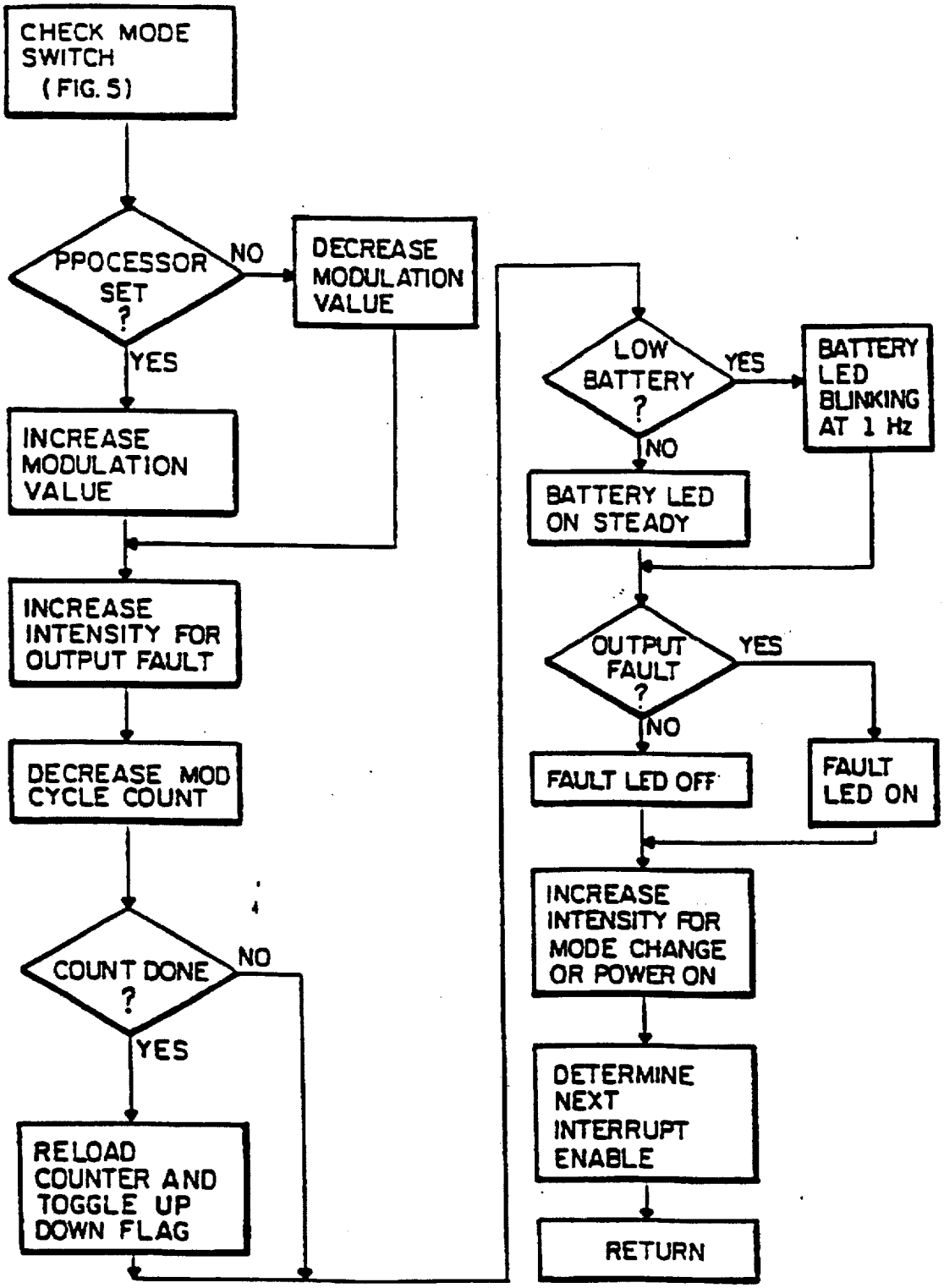
Figure 5:
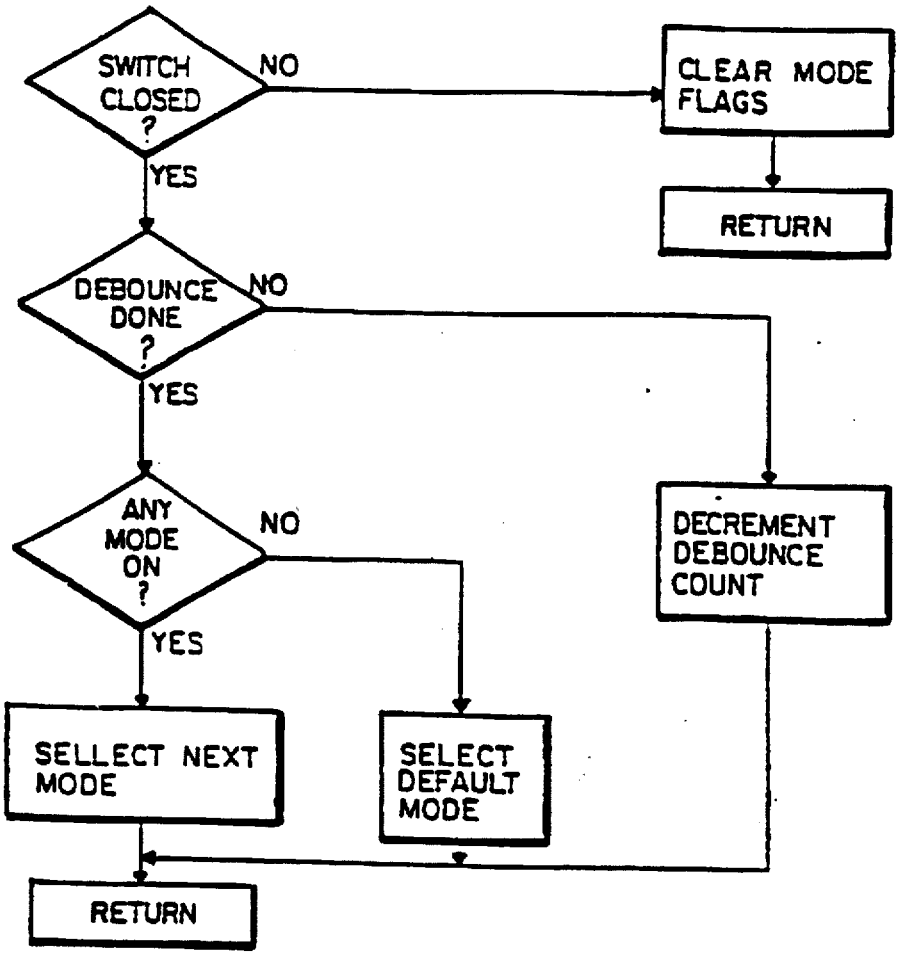

The implementation of the algorithms used in microcomputer 9 (as illustrated in FIGS. 3 through 5) requires the use of the sample-and-hold circuit to measure the output transistor saturation during pulses for each channel (the circuit is necessary only where the pulse rate of the TENS unit is variable since, if the rate is fixed, a simple R-C averaging circuit attached to the analog control transistor drain could produce an appropriate voltage value proportional to the drain voltage during the pulses).

The flow chart, as shown in FIG. 3, provides a test for output errors, the flow chart, as shown in FIG. 4, provides for control of the intensity of the delivered output pulses (preferably every ten milliseconds), and the flow chart, as shown in FIG. 5, provides for mode selection (an intermittent lead routine may also be utilized and differs from the reset routine illustrated in that the intensity is reset to zero and ramp-up requires 2.55 seconds, which is 255 steps of 1/100 second).

The algorithm is initiated by unit reset, change of operating mode, or intermittent lead detection.

When the unit is reset, the initialization of the processor (i.e., the micro-computer) includes slow "ramping" of the intensity setting up to the intensity set by the externally accessible intensity control over a period of 2 seconds. The actual intensity is reset to a binary multiplier factor of "55", which is about 20% of full scale. Then the intensity is ramped up to "255", which is equivalent to a multiplier of 100% of full scale. So whenever the processor resets, the intensity control (or controls if dual channels are being utilized) is checked, and if it is found that the setting of the control, or controls, is at a significant level, then the intensity is ramped slowly up to that level.

Similarly, whenever a change in the mode status is detected, the same two second algorithm is implemented.

Intermittent leads require the most complicated detection algorithm. The algorithm looks for the combination of hard saturation of the output transistors plus greater than 95% of the maximum output voltage from the high voltage inverter power supply (where used in a unit having power conservation that requires monitoring of the saturation of the output transistors, saturation alone would not be a sufficient definition for open electrode leads). An open lead pair means that the supply voltage is at maximum and the output transistor is fully saturated.

To measure the drain voltage of the output transistor, the output stage analog control transistor drain is monitored by sample-and-hold circuit 71, as shown in FIG. 2. Transistor 69 is gated on by the micro-computer during pulses to sample the drain voltage, and this voltage is stored in capacitor 79 until read by A/D converter 19. The drain voltage is converted into binary values from 0 to 255.

Sample and hold circuit 71 measures the drain voltages only in the vicinity of saturation. Drain voltages above about 5 volts are defined as not saturated and produce a maximum A/D output of 255 binary. As can be appreciated from the circuit diagram of FIG. 2, the connection to sample and hold circuit 71 becomes operative only when the drain voltage falls below 5 volts and diode 67 is forward biased.

Micro-computer 9 sees a range of saturation voltages from 0 to 255 binary. A voltage of less than "32" is defined as "hard saturation" while a value of less than "128" is defined as a high impedance electrode circuit. If the value is less than "32", the soft start reset and ramp sequence is started. However, if the value is just less than "128", then an electrode alert light (if utilized) is energized and the reset/ramp sequence is not started. An alert light indication indicates that leads and/or electrodes have too high an impedance and that the user should recheck the electrode system for such things as continuity and moist skin contact.

Output pulse compensation is also automatically provided to maintain the charge delivered per pulse substantially constant when a change occurs in the pulse width of the output pulses then being provided by the device.

Figure 6:
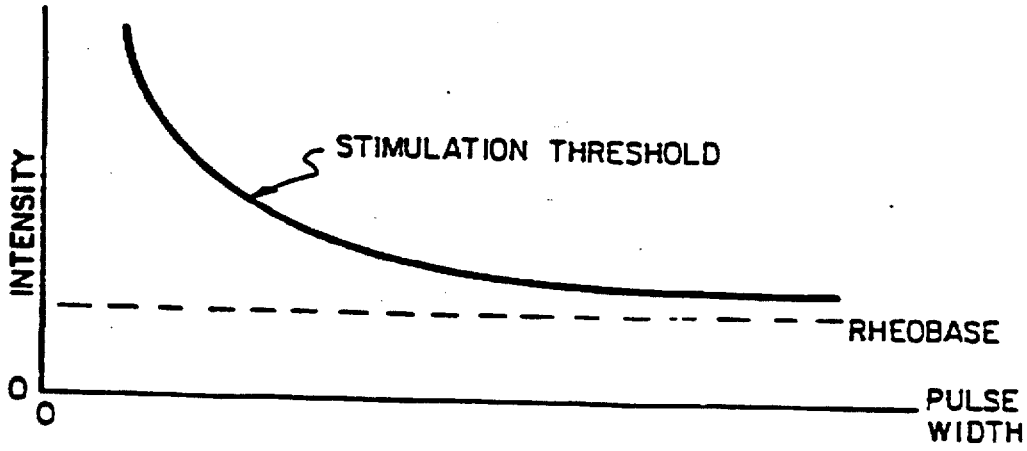
FIG. 6 is a graph of a typical nerve fiber strength-duration curve.

To accomplish such compensation the range of the amplitude, or intensity, of the delivered output pulses is adjusted based upon a nerve fiber strength-duration curve, such as illustrated in FIG. 6.

The curve shown in FIG. 6 illustrates the relationship between the amplitude and the width and the resulting capability to stimulate the nerve fiber. From this curve, it can be seen that if the pulses have too low an amplitude (i.e., less than the "rheobase"), the nerve will never be stimulated, even if the pulse width lasts to infinity.

Pulse width compensation includes, basically, using an applicable strength-duration curve to vary the range of the peak current delivered as pulses from the device. In other words, the pulse width, as then set, determines the peak current range of the intensity control. For every pulse width, there is a corresponding current range for the intensity control.

Figure 7:
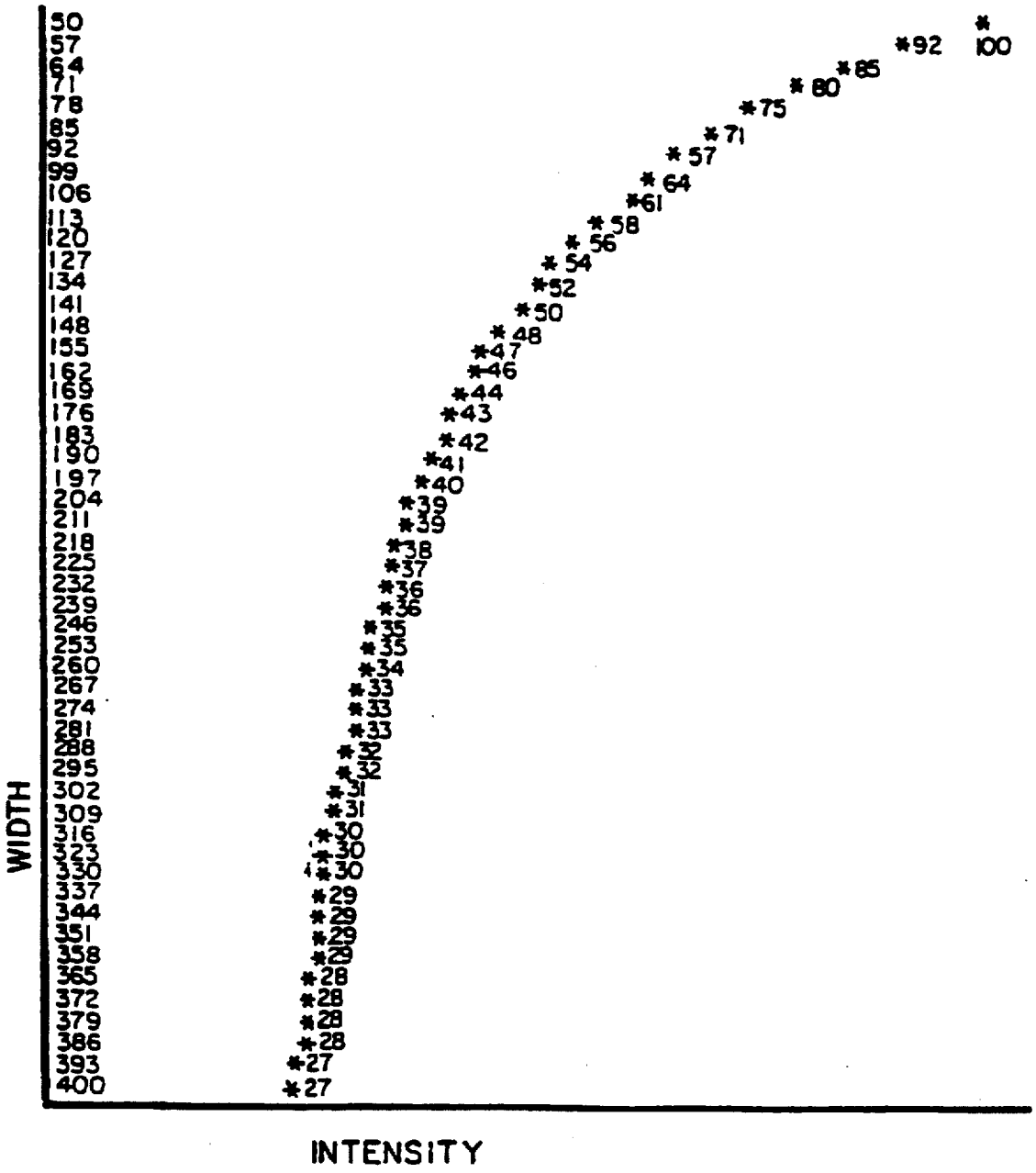
FIG. 7 is a plot of a strength-duration look-up table based upon the strength-duration curve of FIG. 6.

The strength-duration curve shown in FIG. 6 is preferably implemented with a look-up table that can be read by micro-computer 9 and an illustration of such a table, based upon the curve shown in FIG. 6, is set forth in FIG. 7. As illustrated in FIG. 7, at a 50 microsecond pulse width, the intensity is automatically assigned a range of 0 to 100 milliamperes peak, while at 400 microseconds width, the assigned range is 0 to 27 milliamperes peak.

The table, as shown in FIG. 7, was determined imperically and has the following mathematical formula:

$$I=19.6/(1-e(-0.00305\times PW-0.0664)),$$

where I is current and PW is pulse width.

Figure 8A:
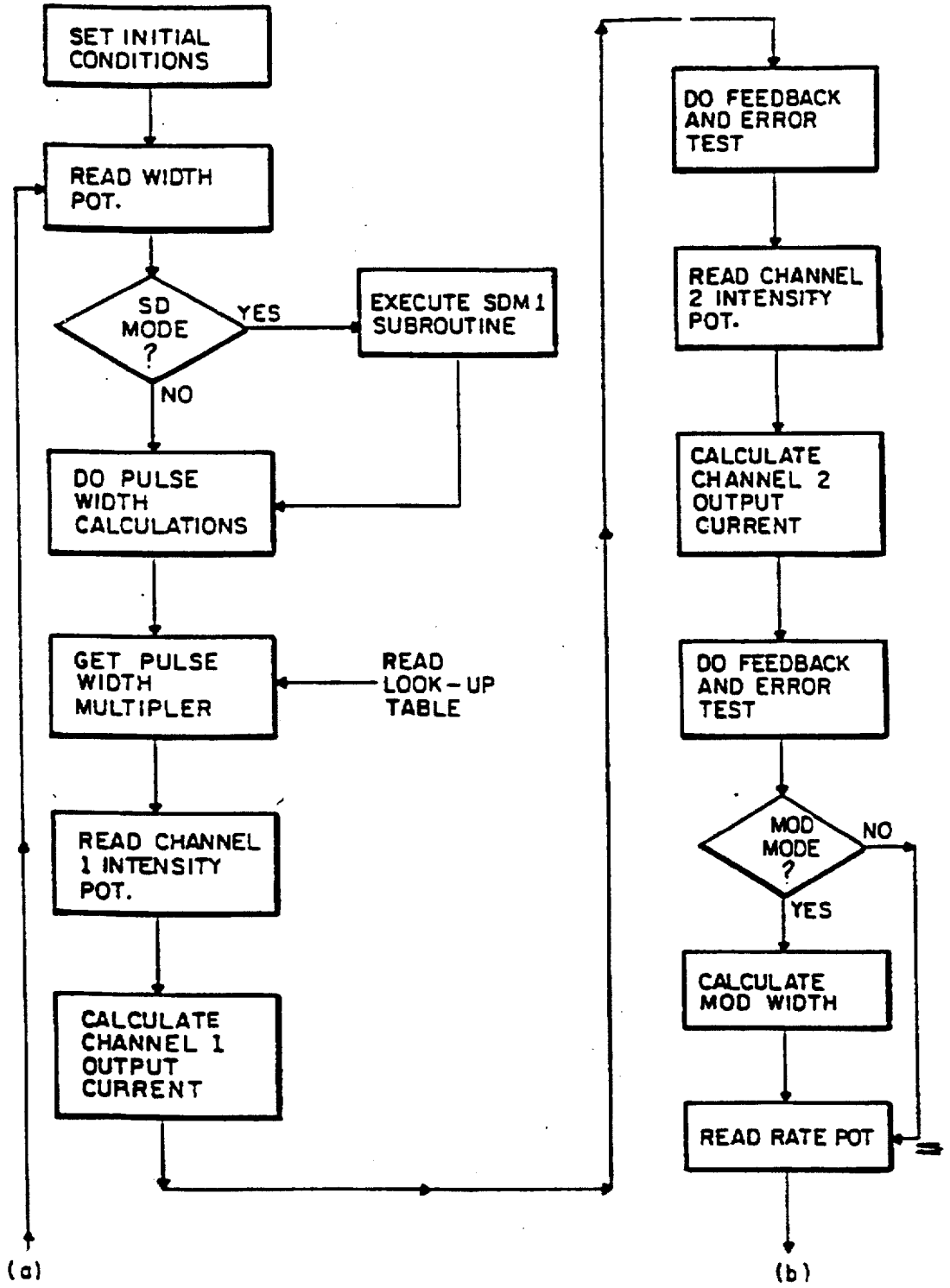
FIGS. 8A and 8B show a flow chart illustrating operation of the micro-computer shown in FIG. 1 to effect output pulse compensation by varying the range of intensities of the output pulses due to pulse width adjustment.
Figure 8B:
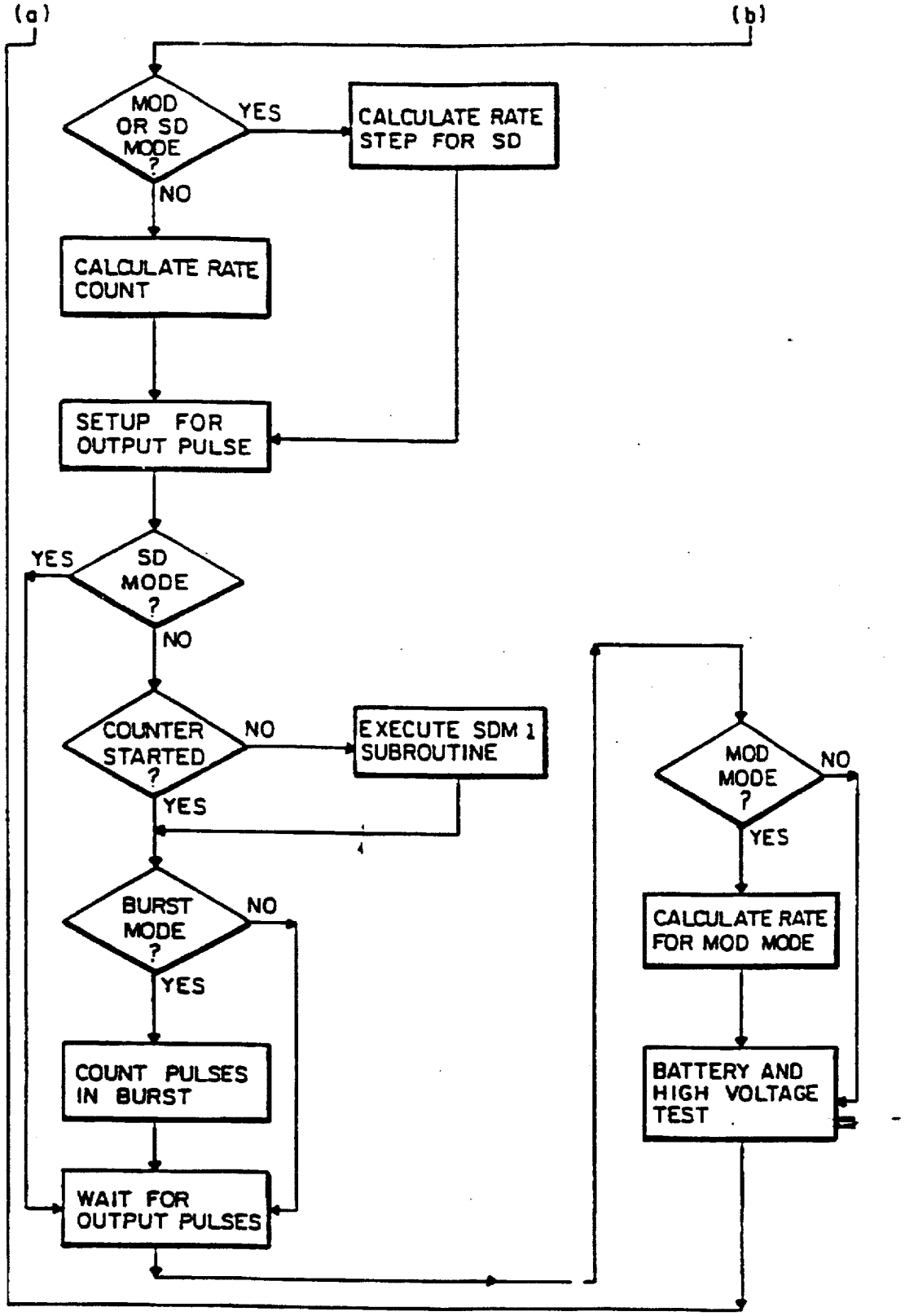

Whenever a new pulse width is selected by the pulse width control the micro-computer, following the thus established algorithm, determines the appropriate range of current (within which range the intensity varying, or controlling, unit (such as a potentiometer) can operate), and then generates the proper reference voltage within that current range for that pulse width. A flow chart illustrating operation of the micro-computer to effect pulse width compensation is set forth in FIG. 8.

After the determination is made at micro-computer 9, the binary number produced is coupled through D/A converter 39 to generate a reference voltage to be coupled to operational amplifier 41.

Thus, the reference voltage equals the setting percentage (of the intensity control potentiometer) x maximum peak current x K, where K is a scale factor that converts the value to the correct binary number and subsequent voltage for the particular device design.

Because the look-up table establishes a range of the intensities, there is, of course, a family of numerous strength curves *one* for each possible intensity percentage setting. This enables smooth control and is normally no more distinguishable to a user than is generating the reference voltage directly using a simple potentiometer.

The look-up table, as shown in FIG. 7, is not suitable for all pulse shapes since this table was derived for use with an asymmetrical biphasic pulse generated by a capacitive output stage which has an active charge bleeder circuit, such as is commonly found in TENS-type units. In such a unit, the active bleeder circuit discharges the charge stored in the output capacitors and tissues during the brief rectangular pulses. When the pulse width is narrow and pulse rate is low, the charge can be dissipated with a simple resistor. However, when wide pulses and high pulse rates are used, the bleeder must actively discharge the capacitance by turning on a bleeder transistor between pulses. The time constant and response characteristics of the bleeder circuit partly determine the exact shape of the look-up table curve.

As an example of how the look-up table might need to be changed, when a bleeder circuit is used that discharges the capacitance more slowly, the curve that produces equal sensation is different and has the following mathematical formula:

$$I=28.125/(1-e(-0.0046389\times PW-1)).$$

The equation has the same form as before, but the rheobase has been shifted to account for the different pulse shape.

For other embodiments of the invention, it would be possible to perform the calculation using the exponential formula every time the pulse width changes. In practice, however, this method appears to be slow, due to the complicated operation, and difficult to implement, at least using an 8 bit micro-controller. It would also be possible to build a compensation control system using analog curve fitting techniques, but this method would appear to require tuning with multiple trim pots and therefore be far more costly.

In practice, a device with output pulse compensation, such as illustrated in FIG. 1, operates in the same manner as does a conventional TENS device, except that compensation is automatically provided by the microcomputer each time the pulse width is changed.

The use of such pulse width compensation will not normally be noticed by a user, particularly since the user is automatically protected, including protection against shock which could otherwise occur, for example, when a large pulse width is selected.

Using pulse width compensation, it is possible to adjust pulse widths while the device is in use and directly compare different pulse widths independent of the intensity (since the percentage of intensity is maintained constant unless the intensity control is also adjusted). Also, the ability to finely control intensity when utilizing wide pulse widths makes exceptionally wide pulse widths practical for use in a general purpose TENS unit or a muscle stimulator unit.

Automatic compensation of the pulse intensity range of the delivered output pulses is achieved as the pulse width is varied. Thus, the pulse height is automatically varied whenever the pulse width is changed to hold the amplitude of sensation constant.

Without an arrangement to automatically vary the intensity control potentiometer (which normally has an externally visible indicator associated therewith), the actual intensity being delivered cannot be correctly portrayed at the intensity control indicator for each of a plurality of pulse widths. The range of intensities is thus changed as the pulse width is changed. The intensity control potentiometer indicator therefore acts as a percentage indicator that consistently indicates whatever percent of the intensity range is then selected by the intensity control potentiometer. Thus, amplitude is defined as a family of strength-duration curves, with each curve representing a separate setting of the intensity control.

As can be appreciated from the foregoing, this invention provides improved output pulse compensation for an electronic device providing a pulse output for therapeutic purposes.

What is claimed is:

1. An electronic device for providing output pulses *to a user* for therapeutic purposes, said device comprising:

electronic controller means *for* providing control pulses;

voltage supply means *for* providing a voltage output;

pulse output means including transistor means for receiving said control pulses and said voltage output and, responsive thereto, providing output pulses for therapeutic purposes having an intensity *level* and *a* pulse width subject to change due to the occurrence of predetermined condition variations; and said electronic controller means including sensing means connected with said transistor means for sensing saturation of said transistor means indicative of the occurrence of [a] *one of the* predetermined condition [variation] *variations* capable of causing user discomfort while said output pulses are being provided, and, responsive thereto, said electronic controller means causing intensity compensation of said output pulses by causing the intensity *level* of said output pulses to be quickly reduced to a predetermined intensity level and then, upon completion of said reduction, causing the intensity level of said output pulses to be gradually increased toward the intensity level of said output pulse existing immediately prior to sensing of the occurrence of said predetermined condition variation.

2. The device of claim 1 wherein said electronic controller means allows the intensity level of said output pulses to be gradually increased over a predetermined period of time *toward said prior existing level* unless said electronic controller means senses the occurrence of [a] *one of the* predetermined condition [variation] *variations* capable of causing user discomfort during said predetermined time period of gradual increase of the intensity level of said output pulses.

3. The device of claim 1 wherein said electronic controller means includes micro-computer means for causing generation of said control pulses and for effecting said intensity compensation of said output pulses.

4. An electronic device for providing output pulses for therapeutic purposes, said device comprising:

electronic controller means *for* providing control pulses;

voltage supply means *for* providing a voltage output;

pulse output means for receiving said control pulses and said voltage output and, responsive thereto, providing output pulses for therapeutic purposes having an intensity and *a* pulse width [subject to change due to the occurrence of predetermined condition variations], *said intensity being variable within a range of intensities, wherein the range of intensities has a maximum intensity that is based on the pulse width in a strength-duration curve relationship and wherein said intensity equals a variable percentage of the maximum intensity*;

pulse width control means for varying the *pulse* width of said output pulses;

intensity percentage control means for varying the percentage of *the maximum* intensity [of] *for* said output pulses; and said electronic controller means including sensing means for sensing a predetermined condition variation [establishing] *that is indicative of* a change in the *pulse* width of the output pulses [by said pulse width control means], and, responsive thereto, causing a corresponding [and predetermined] change in the range of intensities [of said output pulses] based upon [a] *said* strength-duration curve [applicable to said output pulses, said] *and causing a* change in the [range of intensities] *intensity* of said output [pulses being] *pulse* in a manner such that *the intensity of the output pulse is substantially maintained at* the percentage of *the maximum* intensity as [established] *varied* by said intensity percentage control means [is substantially maintained].

5. The device of claim 4 wherein *each of said output pulses delivers a charge that has a resulting capability to stimulate nerve fiber, and* said electronic controller means causes said corresponding [and predetermined] change in the range of intensities [of said output pulses] to be such that *the resulting capability to stimulate nerve fiber of* the charge [delivered per pulse] of said output pulses is maintained substantially constant.

6. In an electronic device for providing output pulses *having a variable intensity level* for therapeutic purposes and having output means for producing said pulses that includes a transistor with a drain *having a drain voltage*, output pulse compensation means comprising first means including sensing means connected with said output means for sensing the drain voltage of said transistor indicative of a change in at least one predetermined condition being then monitored and sample and hold means connected with said sensing means whereby said sample and hold means receives the sensed drain voltage of said transistor, and second means connected with said sample and hold means for causing a rapid decrease in the intensity level of said output pulses upon sensing of said change in at least one predetermined condition being then monitored, said second means, upon completion of said rapid decrease in intensity level, then causing the intensity level of said output pulses to be thereafter gradually increased over a predetermined time period toward the intensity level of said output pulses existing immediately prior to said rapid decrease.

7. The device of claim 6 wherein said compensation means causes said rapid decrease in the intensity level of said output pulses in response to a predetermined change condition capable of causing user discomfort or possible injury.

8. The device of claim 6 wherein said sample and hold means includes capacitor means for storing a voltage indicative of said sensed change in said predetermined condition being then monitored.

9. The device of claim 6 wherein said compensation means causes said gradual increase in the intensity level of said output pulses over a period of about two seconds.

10. An electronic device for providing output pulses for therapeutic purposes, said device comprising:

electronic controller means *for* providing control pulses;

voltage supply means forproviding a voltage output;

pulse output means for receiving said control pulses and said voltage output and, responsive thereto, providing output pulses *having an intensity level* for therapeutic purposes, said pulse output means including transistor means *having a drain with a drain voltage*; and said electronic controller means including sample and hold means connected with said transistor means for sensing the drain *voltage* of said transistor means and capacitor means for storing a voltage indicative of said drain *voltage*, said electronic controller means receiving said voltage stored at said capacitor means and, responsive to [a] *an amount of* stored voltage indicative of the occurrence of a predetermined condition variation, causing intensity compensation of said output pulses by rapidly decreasing the intensity level of said output pulses and thereafter gradually increasing the intensity level of said output pulses over a predetermined period of time toward the intensity level of said output pulses existing immediately prior to said rapid decrease in intensity level.

11. The device of claim 10, wherein said transistor means is an analog control output transistor, and wherein said sample and hold means includes a gate transistor connected between said analog control output transistor and said capacitor means.

12. In an electronic device for providing [a pulse] output [signal] *pulses* for therapeutic purposes [with], *each of said output pulses having a pulse width and intensity*, said electronic device having pulse width control means for varying the pulse width of said [pulse] output [signal] *pulses* and intensity [percentage] control means for varying the [percentage of] intensity of said output pulses, [pulses] *to produce a charge for each output pulse that has a resulting capacity to stimulate nerve fiber pulse* width compensation means comprising:

*intensity percentage control means for variably setting a percentage of a maximum intensity for the intensity of the output pulses, wherein said maximum intensity is defined by a strength-duration curve relationship between pulse width and intensity for nerve fiber stimulation capability such that there is a range of intensities limited by the maximum intensity for a pulse width;* sensing means for sensing a change in the pulse width [of said pulse output signal] by said pulse width control means and providing an output indicative thereof; and electronic means for causing a change in the *intensity and in the* range of intensities of said [pulse] output [signal] *pulses* responsive to said output from said sensing means, with said change in the *intensity and in the* range of intensities of said [pulse] output [signal] *pulses* being in a manner such that *the intensity of said output pulses is substantially maintained at* the percentage of *maximum* intensity *in the range of intensities* as [established] *varied* by said intensity percentage control means [is substantially maintained], and with said change in the range of intensities of said pulse output signal being based upon [a] *the* strength-duration curve applicable to said [delivered] *output* pulses [of said pulse output signal to thereby maintain] *such that the resulting capability to stimulate nerve fiber of* the charge [delivered per] *for each* pulse [of said pulse output signal] *is maintained* substantially constant.

13. The pulse width compensation means of claim 12 wherein said electronic means of said pulse width compensation means is a part of a micro-computer controlled by a predetermined algorithm.

14. The pulse width compensation means of claim 13 wherein said electronic device is a TENS-type unit, and wherein said preselected algorithm follows a mathematical formula of $I=19.6/(1-e^{(-0.00305\times PW-0.0664)})$, where I is current and PW is pulse width.

15. An electronic device for providing output pulses for therapeutic purposes, *each of which output pulses has a pulse width and intensity to produce a charge for each output pulse that has a resulting capability to stimulate nerve fiber,* said device comprising:

pulse width control means *for varying the pulse width of said output pulses, wherein the intensity of the output pulses is variable within a range of intensities, and wherein the range of intensities has a maximum intensity that is based on the pulse width in a strength-duration curve relationship*;

[amplitude] *intensity* percentage control means *for varying the percentage of the maximum intensity for said output pulses*;

controller means connected with said pulse [with] *width* control means and said [amplitude] *intensity* percentage control means, said controller means providing control pulses, each [pulse] of which *control pulses* has a width and an [amplitude] *intensity* determined by said pulse width control means and said [amplitude] *intensity percentage* control means;

high voltage supply means for providing a high voltage output;

pulse output means for receiving said control pulses and said high voltage output and, responsive thereto, providing output pulses for therapeutic purposes; and said controller means also providing pulse compensation for causing a change in the range of intensities [of said output pulses] responsive to a variation in said pulse width of said output pulses [effected by said pulse width control means], with said change in the range of intensities [of said output pulses] being based upon [a] *said* strength-duration curve [applicable to said delivered output pulses to thereby maintain] *relationship such that the resulting capability to stimulate nerve fiber of* the charge [delivered per pulse] *for each* of said output pulses *is maintained* substantially constant and [with the] *causing a* change in the range of intensities of said output pulses responsive to variation in pulse width [being] in a manner such that *the intensity of each output pulse is substantially maintained at* the percentage of *the maximum* intensity [established] *as varied* by said [amplitude] *intensity* percentage control means [is substantially maintained] so that the intensity [level delivered] within said range of intensities is such that the [delivered] charge *that stimulates nerve fiber* remains unchanged by a change in *pulse width by* said pulse width control means.

16. The device of claim 15 wherein said device provides output pulses to a plurality of output channels, and wherein said pulse compensation is provided for each of said output channels.

17. The device of claim 16 wherein said device includes a separate [amplitude] *intensity percentage* control means for each of said output channels, with each of said [amplitude] *intensity percentage* control means providing a separate percent of intensity control for each said channel.

18. A method for providing output pulses for therapeutic purposes, said method comprising:

providing control pulses;

providing a voltage output;

providing an output *means* having transistor means for receiving said control pulses and said voltage output and, responsive thereto, providing output pulses having an intensity *level* and a pulse width subject to change due to the occurrence of predetermined condition variations;

sensing the occurrence of saturation of said transistor means indicative of [a] *one of the* predetermined condition [variation] *variations* capable of causing user discomfort while said output pulses are being provided; and utilizing said sensed occurrence of said predetermined condition variation to cause intensity compensation of said output pulses by causing the intensity *level* of said output pulses to be quickly reduced to a predetermined intensity level and then upon completion of said reduction, causing the intensity level of said output pulses to be gradually increased toward the intensity level of said output pulses existing prior to sensing of the occurrence of said predetermined condition variation.

19. The method of claim 18 wherein said method includes allowing the intensity level of said output pulses to be gradually increased over a predetermined period of time *toward said prior existing level* unless the occurrence of [a] *one of the* predetermined condition [variation] *variations* capable of causing user discomfort is sensed during said predetermined time period of gradual increases of the intensity level of said output pulses.

20. A method for providing output pulses for therapeutic purposes, said method comprising:

providing control pulses;

providing a voltage output;

receiving said control pulses and said voltage output and, responsive thereto, providing output pulses having an intensity and pulse width [subject to change due to the occurrence of predetermined condition variations] *that produces a charge that has a resulting capability to stimulate nerve fiber, said intensity being variable within a range of intensities, wherein the range of intensities has a maximum intensity that is based on the pulse width in a strength-duration curve relationship and wherein said intensity equals a variable percentage of the maximum intensity*;

[providing pulse width control means for] varying the *pulse* width of said output pulses;

[providing intensity percentage control means for] varying the percentage of *the maximum* intensity [of] *for* said output pulses; and sensing of a predetermined condition variation [established by varying] *that is indicative of a variation in* the

*pulse* width of the output pulses [by said pulse width control means], and responsive thereto, causing [the] *a* corresponding [and predetermined] change in the range of intensities [of said output pulses] based upon [a] *said* strength-duration curve [applicable to said output pulses, said] *and causing a* change in the [range of intensities] *intensity* of said output pulses [being] in a manner such that *the intensity of the output pulses are substantially maintained at* said percentage of *the maximum* intensity as [established] *varied* by said intensity percentage control means [is substantially maintained].

21. The method claim 20 [wherein said provided pulse compensation causes] *including to step of causing* said corresponding [and predetermined] change in the range of intensities of said output [pulse] *pulses* to be such that *the resulting capability to stimulate nerve fiber of* the charge [delivered] per *output* pulse [of said output pulses] is maintained substantially constant.

22. A method for providing output pulse compensation in an electronic device providing output pulses *having a variable intensity level* for therapeutic purposes and having output means that includes a transistor with a drain *having a drain* voltage, said method comprising:

providing sensing means for sensing the drain *voltage* of said transistor of said output means indicative of a change in at least one predetermined condition being then monitored;

providing sample and hold means for receiving the sensed drain voltage of said transistor indicative of said change in said predetermined condition then being monitored; and causing a rapid decrease in the intensity level of said output pulses upon sensing of said change in said predetermined condition and then, upon completion of said decrease of intensity level, gradually increasing the intensity level of said output pulses over a predetermined time period toward the intensity level of said output pulses existing immediately prior to said rapid decrease.

23. The device of claim 22 wherein said method includes causing said rapid decrease in the intensity level of said output pulses in response to a predetermined changed condition capable of causing user discomfort or possible injury.

24. The method of claim 22 wherein said gradual increase in the intensity level of said output pulses occurs over a period of about two seconds.

25. A method for providing pulse width compensation in an electronic device providing output pulses for therapeutic purposes, *wherein each of the pulses has an intensity and a pulse width that produces a charge that has a resulting capability to stimulate nerve fiber,* said method comprising:

establishing a percentage of *maximum* intensity *of the output pulses* within a range of intensities, *wherein the range of intensities has a maximum intensity that is based on the pulse width in a strength-duration curve relationship and wherein the intensity equals the established variable percentage of the maximum intensity*;

[sensing] *determining* a change in the *pulse* width of the output pulses [being then delivered];

determining a new range of intensities *with a new maximum* based upon [a] *said* strength-duration curve *relationship* for said output pulses that corresponds to said change in pulse width; and providing output pulses having changed pulse width with said output pulses having said established percentage of *maximum* intensity within said [then determined] range of intensities of said output pulses maintained [to thereby also maintain] *such that the resulting capability to stimulate nerve fiber of* the charge [delivered per pulse] of said output pulses *is maintained* substantially constant.

26. The method of claim 25 wherein said method includes changing the percentage of [the amplitude] *maximum intensity* of said delivered pulses independent of any said pulse width change of said delivered pulses.

27. The method of claim 25 wherein said electronic device is a TENS type unit, and wherein said change of said range of intensities follows the mathematical formula of $I=19.6/(1-e^{(-0.00305\times PW-0.0664)})$, where I is current and PW is pulse width.

* * * * *